(12) United States Patent
Nibhanipudi (10) Patent No.: US 11,413,183 B2
(45) Date of Patent: Aug. 16, 2022

(54) DOUBLE SOFT CERVICAL COLLAR AND METHOD OF USE THEREOF

(71) Applicant: Kumara Venkatanarayana Nibhanipudi, Scarsdale, NY (US)

(72) Inventor: Kumara Venkatanarayana Nibhanipudi, Scarsdale, NY (US)

(*) Notice: Subject to any disclaimer, the term of this patent is extended or adjusted under 35 U.S.C. 154(b) by 412 days.

(21) Appl. No.: 16/739,641

(22) Filed: Jan. 10, 2020

(65) Prior Publication Data

US 2020/0222223 A1    Jul. 16, 2020

Related U.S. Application Data

(63) Continuation-in-part of application No. 14/980,595, filed on Dec. 28, 2015, now abandoned.

(30) Foreign Application Priority Data

Jan. 2, 2015   (IN) ............................... 34/CHE/2015

(51) Int. Cl.
   *A61F 5/055*   (2006.01)

(52) U.S. Cl.
   CPC .................................. *A61F 5/055* (2013.01)

(58) Field of Classification Search
   CPC .. A61F 5/055; A61F 5/05883; A61F 5/05891; A61F 5/3707; A61F 2250/0004; A61F 5/01; A61F 2250/001; A61F 13/12; A61F 2007/0009; A61F 2007/001; A61F 2007/0228; A61F 2007/0231; A61F 2250/0003; A61F 5/024; A61F 5/042; A61F 5/05; A61F 5/058; A61F 5/05816; A61F 5/05825; A61F 5/30; A61F 5/56; A61G 13/121; A61G 13/1215; A61G 7/07; A61G 7/072; A47C 7/38
   See application file for complete search history.

(56) References Cited

U.S. PATENT DOCUMENTS

| | | | |
|---|---|---|---|
| 3,135,256 A | 6/1964 | Gruber | |
| 3,189,026 A | 6/1965 | Barnett | |
| 4,205,667 A | 6/1980 | Gaylord, Jr. | |
| 4,422,454 A | 12/1983 | English | |

(Continued)

FOREIGN PATENT DOCUMENTS

WO   1991004719 A1   4/1991

OTHER PUBLICATIONS

Office Action issued in corresponding Indian Patent Appln. 34/CHE/2015, dated Sep. 28, 2020.

(Continued)

*Primary Examiner* — Ophelia A Hawthorne
(74) *Attorney, Agent, or Firm* — Blue Filament Law PLLC (57) ABSTRACT

A method of using a double soft cervical collar including placing a first soft cervical collar around a neck of a wearer; securing the first soft cervical collar around the neck of a wearer with a sticky portion that extends from a first end of the first soft cervical collar and attaches to a second end of the first soft cervical collar; placing a second soft cervical collar surrounding the first soft cervical collar; and securing the second soft cervical collar surrounding the first soft cervical collar with a sticky portion that extends from a first end of the second soft cervical collar and attaches to a second end of the second soft cervical collar.

20 Claims, 4 Drawing Sheets

(56) References Cited

U.S. PATENT DOCUMENTS

| | | | | |
|---|---|---|---|---|
| 4,966,136 | A | * | 10/1990 | Bates .................... A61F 5/3738 |
| | | | | 602/18 |
| 5,029,577 | A | * | 7/1991 | Sarkozi .................. A61F 5/055 |
| | | | | 602/18 |
| 5,334,133 | A | | 8/1994 | Carroll |
| 5,788,658 | A | | 8/1998 | Islava |
| 7,320,671 | B2 | * | 1/2008 | Gerstmar ................ A61F 5/055 |
| | | | | 602/18 |

OTHER PUBLICATIONS

Carter, V.M. et al. "The effect of a soft collar, used as normally recommended or reversed, on three planes of cervical range of motion", Journal of Orthopaedic & Sports Physical Therapy, Mar. 1996, vol. 23, No. 3, pp. 209-215.

Miller, C.P. et al. "Soft and rigid collars provide similar restriction in cervical range of motion during fifteen activities of daily living", SPINE, Jun. 1, 2010, vol. 35, No. 13, pp. 1271-1278.

Muzin, S. et al. "When should a cervical collar be used to treat neck pain?", Curr Rev Musculoskelet Med., Jun. 2008, published online on Dec. 12, 2007, vol. 1, pp. 114-119.

Nibhanipudi, K. "A Study To Compare the Usefulness of Double Soft Cervical Collar Versus Hard Cervical Collar (Philadelphia Collar) For Neck Immobilization", The Internet Journal of Emergency and Intensive Care Medicine, Oct. 9, 2014, vol. 14, No. 1, 7 pages.

U.S. Appl. No. 14/980,595, filed Dec. 28, 2015.

* cited by examiner

DOUBLE SOFT CERVICAL COLLAR AND METHOD OF USE THEREOF

RELATED APPLICATIONS

This application is a continuation-in-part of U.S. application Ser. No. 14/980,595 filed Dec. 28, 2015 that in turn claims priority benefit of Indian Application Serial No. 34/CHE/2015 filed Jan. 2, 2015; the contents of which are hereby incorporated by reference.

FIELD OF THE INVENTION

The present invention relates to medical devices in the field of Emergency and Intensive Care Medicine. The present invention particularly discloses a method of use of a double soft cervical collar. The present invention also particularly relates to the usefulness of a double soft cervical collar over hard (Philadelphia collar) and soft cervical collars.

BACKGROUND OF THE INVENTION

The neck consists of bones, muscles and ligaments. Any abnormality, inflammation, strain, injury, or trauma can cause neck pain. Neck pain is seldom a debilitating condition, though it can indicate serious underlying physiological or pathological conditions when it extends beyond a week.

In either case, cervical collars are one of the basic prescriptions used to treat neck pain besides analgesics. Cervical collars, which are orthopaedic medical devices, are preferred for the mere reason of physical support and also as an effective way to facilitate immobility of the neck in an effort to reduce further trauma, realign the spinal cord, and thus relieve pain. However, cervical collars are not recommended to be worn for long periods of time.

Cervical collars are of two main types—hard (Philadelphia collar) and soft.

Hard cervical collars, on one hand, are rigid and are wrapped tightly around the neck. They find specific use in Emergency Medicine after severe trauma, surgery, cervical fractures, or dislocations because they are highly restrictive of neck movements. On the other hand, hard cervical collars can cause adverse effects illustratively including exacerbation of pain, breath restrictions, tissue ischemia, and increased risk of aspiration when worn continuously over an extended period of long time. Hard cervical collars can also present difficulty in nursing care and discomfort to the patient.

Soft cervical collars are a contrast to hard cervical collars. They are flexible with contours that facilitate easy alignment around the neck. They are soft when wrapped around the neck and do not give a tightened feeling around the neck and hence, are the most comfortable cervical collars for a patient to wear. Soft cervical collars are, however, less restrictive of neck movements relative to hard cervical collars, and their scope of use is limited to less serious conditions like neck strain, sprain, whiplash injury, or chronic neck pain that can be caused by varying reasons. Soft cervical collars are cheaper compared to hard cervical collars.

In an article published in *Curr Rev Musculoskelet Med.* in June 2008; 1(2): 114-119 published online on Dec. 12, 2007. doi: 10.1007/s12178-007-9017-9, titled 'When should a cervical collar be used to treat neck pain?', authored by Stefan Muzin et al., it was disclosed that while hard collars were an important part of acute injury and spine stabilization, they were not routinely used to manage pain because of severe adverse effects of prolonged use.

In an article published in the *J Orthop Sports Phys Ther.* in 1996 March; 23(3):209-15, titled 'The effect of a soft collar, used as normally recommended or reversed, on three planes of cervical range of motion', authored by Carter V M, et al., it was stated that soft collars, recommended to immobilize the cervical spine following trauma, could be used in a normal manner, secured at the back of the neck of a patient, or a reversed manner, secured at the front of the neck of a patient, the latter method being useful to achieve limitation of mobility in a specific direction without drastic differences in the extent of neck movement immobilization. The study for investigating the effectiveness of soft cervical collars in limiting cervical range of motion was stated to be done on 50 healthy volunteers using the Orthopaedic Systems Inc. Computerized Anatometry-6000 Spine Motion Analyzer in six ranges of motion under three conditions: no collar, recommended use, and reversed manner. It was disclosed that the post hoc paired t tests showed that wearing the collar either as recommended in a normal manner or in a reversed manner, decreased motion compared with not wearing a collar, and that the position of the collar affected range of motion in three of the six motions. The differences in range were attributed to location of the collar closure and initial head posture. The soft cervical collar restricted motion when worn either way.

It was disclosed in prior art that rigid cervical collars were generally used to reduce cervical motion to a greater extent than soft cervical collars, but the latter was preferred by the patients because of their greater comfort. In the article published in *Spine* (Phila Pa. 1976) in 2010 June 1; 35(13): 1271-8. doi: 10.1097/BRS.0b013e3181c0ddad titled 'Soft and rigid collars provide similar restriction in cervical range of motion during fifteen activities of daily living', authored by Miller C P et al., it was stated that there was data suggesting that soft cervical collars restricted full, active ROM (i.e., the extremes of motion), though to a lesser extent than the rigid cervical collars. The article disclosed comparative studies assessing the effects of these two types of cervical collars on the functional ROM that is required to perform multiple activities of daily living. It was concluded that though the subjects exhibited a less full, active ROM of the cervical spine when a rigid cervical collar was used, there was no significant difference in the motion in nearly all of the activities regardless of which cervical collar was applied. It was suggested that the small difference was due to both cervical collars serving as proprioceptive guides that allow patients to regulate their own cervical motion based on their level of comfort.

The prior art, however, presents a few problems in using hard or soft cervical collars for neck trauma. Hard cervical collars show the highest degree of immobilization of the neck but can also cause adverse effects like tissue ischemia, exacerbation of pain, increased risk of aspiration, etc. Soft cervical collars are flexible and accommodating to the body contours of the patient's neck, thus increasing patient comfort levels, but do not have the necessary rigidity to impart the desired immobility to the neck.

Owing to the adverse effects caused by hard cervical collars and the lack of rigidity associated with single soft cervical collars, there exists a need for novel approach to treating neck trauma that improves patient comfort, protects against secondary injury caused by prior art cervical collars, and ultimately improves patient rehabilitation time and experience, by providing a double soft cervical collar and method of use thereof that combines the useful features of both hard and soft cervical collars.

OBJECTIVE OF THE INVENTION

The objective of the present invention is to provide a method of using a double soft cervical collar that has a combination of desirable properties from both hard and soft cervical collars illustratively including rigidity, similar to a hard cervical collar, and flexibility and softness, similar to a soft cervical collar.

Another objective of the present invention is to compare the usefulness of the inventive double soft cervical collar over single soft and single hard cervical collars.

Yet another objective of the present invention is to show that the effectiveness of the inventive double soft cervical collar is on par or greater than that of a hard (Philadelphia collar) cervical collar.

SUMMARY OF THE INVENTION

The present invention discloses a method of using a double soft cervical collar and demonstrates its usefulness over single hard (Philadelphia collar) and soft cervical collars.

One embodiment of the present invention relates to the method of using the double soft cervical collar comprising wearing a first single soft cervical collar, and a second soft cervical collar, on top of the first soft collar. A first soft cervical collar is placed around the neck of a wearer and secured around the neck of a wearer with a sticky portion that extends from a first end of the first soft cervical collar and attaches to a second end of the first soft cervical collar. A second soft cervical collar is then placed surrounding the first soft cervical collar and secured surrounding the first soft cervical collar with a sticky portion that extends from a first end of the second soft cervical collar and attaches to a second end of the second soft cervical collar.

Another embodiment of the present invention relates to the method of using the double soft collar comprising securing a first single soft cervical collar around the neck of a wearer in a reverse manner with the sticky portion of the first soft cervical collar attached to the second end of the first soft cervical collar at the front of the neck of the wearer, and securing a second soft cervical collar surrounding the first soft cervical collar in a traditional manner with the sticky portion of the second soft cervical collar attached to the second end of the second soft cervical collar at the back of the neck of the wearer.

Another embodiment of the present invention relates to the method of using the double soft collar comprising securing a first single soft cervical collar around the neck of the wearer in a traditional manner with the sticky portion of the first soft cervical collar attached to the second end of the first soft cervical collar at the back of the neck of the wearer, and securing a second soft cervical collar surrounding the first soft cervical collar in a reverse manner with the sticky portion of the second soft cervical collar attached to the second end of the second soft cervical collar at the front of the neck of the wearer.

Another embodiment of the present invention relates to the method of using the double soft collar comprising securing a first single soft cervical collar in a traditional manner with the sticky portion of the first soft cervical collar attached to the second end of the first soft cervical collar at the back of the neck of the wearer, and securing a second soft cervical collar surrounding the first soft cervical collar in a reverse manner with the sticky portion of the second soft cervical collar attached to the second end of the second soft cervical collar at the front of the neck of the wearer, such that the method of using the double soft cervical collar creates a subjective feeling of tightness and inability to move the neck.

Another embodiment of the present invention relates to the method of using the double soft collar comprising securing a first single soft cervical collar in a traditional manner with the sticky portion of the first soft cervical collar attached to the second end of the first soft cervical collar at the back of the neck of the wearer, and securing a second single soft cervical collar surrounding the first soft cervical collar in a reverse manner with the sticky portion of the second soft cervical collar attached to the second end of the second soft cervical collar at the front of the neck of the wearer, such that the method of using the double soft cervical collar creates a subjective feeling of tightness and inability to move the neck, and that the subjective feeling of tightness perceived by the wearer is equal to or greater than the subjective feeling of tightness perceived by a wearer of a hard collar, and the subjective feeling of inability to move the neck perceived by the wearer is equal to or greater than the subjective feeling of inability to move the neck perceived by a wearer of a hard collar.

In yet another embodiment, the present invention relates to the usefulness of the inventive double soft cervical collar in immobilizing the neck similar to or better than a hard cervical collar while being flexible like a single soft cervical collar.

In yet another embodiment, the present invention relates to the usefulness of the inventive double soft cervical collar in being flexible and as soft as a single soft cervical collar while immobilizing the neck similar to or better than a hard cervical collar while being softer than a hard cervical collar.

In yet another embodiment of the present invention, the inventive double soft cervical collar minimizes the risk of causing adverse effects and secondary cervical collar related neck trauma relative to a hard cervical collar and/or a single soft cervical collar.

In yet another embodiment of the present invention, the inventive double soft cervical collar reduces the possibility of adverse effects that are observed in the usage of a hard cervical collar illustratively including tissue ischemia, exacerbation of pain, or increased risk of aspiration.

BRIEF DESCRIPTION OF THE DRAWINGS

The following drawings have been provided along with the detailed description of the present invention by way of illustration only for a better comprehension of various embodiments of the present invention, and thus are not limitative of the present invention, wherein.

DETAILED DESCRIPTION OF THE INVENTION

A method of using an inventive double soft cervical collar 100 in a manner that shows tightness around the neck and immobilizes the neck is provided. It is appreciated that the inventive method of using a double soft cervical collar 100 imparts rigidity equal to or greater than that provided by a single hard cervical collar, and also provides the flexibility and comfort equal to or greater than that provided by a single soft cervical collar. It is further appreciated that the inventive method of using a double soft cervical collar 100 minimizes the risk of causing adverse effects and secondary cervical collar related neck trauma relative to the use of a single hard or soft cervical collar illustratively including tissue ischemia, exacerbation of pain, and increased risk of aspiration.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

Figure 1:
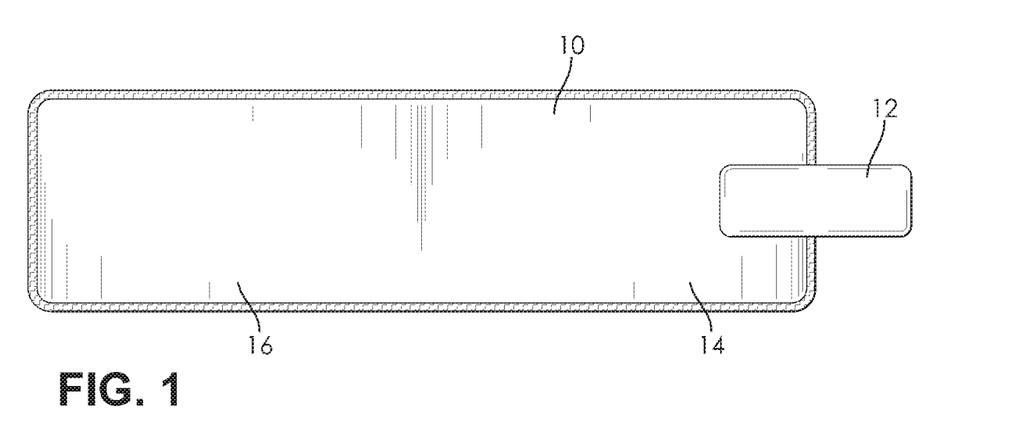
FIG. 1: shows a single first soft cervical collar 10 with a first end 14, a second end 16, and a sticky portion 12 extending from the first end 14 according to embodiments of the invention.
Figure 2:
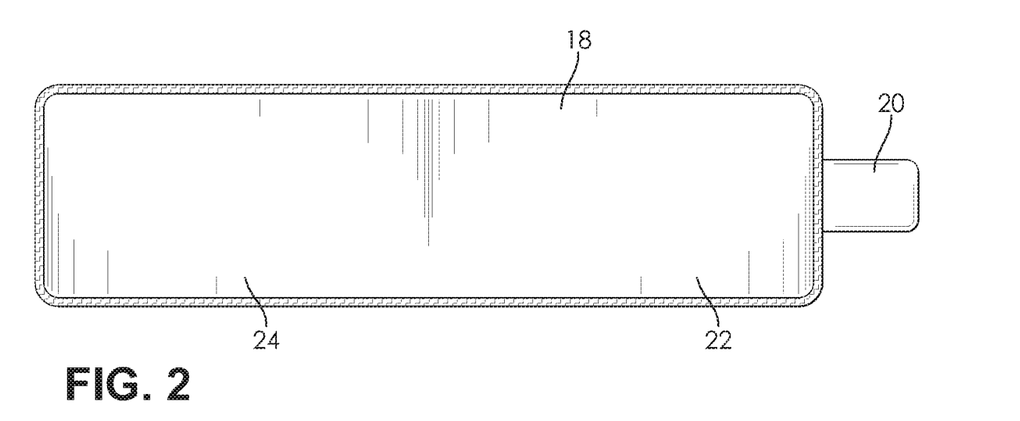
FIG. 2: shows a single second soft collar 18 with a first end 22, a second end 24, and a sticky portion 20 extending from the first end 22 according to embodiments of the invention.

Referring now to the figures, an inventive method of using a double soft collar 100 (shown in FIGS. 3B, 4B, and 5B) is provided. FIG. 1 shows a first soft cervical collar 10 with a sticky portion 12 that extends from a first end 14 of the first soft cervical collar 10 and attaches to a second end 16 of the first soft cervical collar 10. FIG. 2 shows a second soft cervical collar 18 with a sticky portion 20 that extends from a first end 22 of the second soft cervical collar 18 and attaches to a second end 24 of the second soft cervical collar 18. It is appreciated that in some inventive embodiments, the sticky portions 12 and 20 extend between the first ends 14 and 22 of the first and second soft cervical collars 10 and 18, respectively, and then attach to the second ends 16 and 24 of the first and second soft cervical collars 10 and 18, respectively.

As used herein, it is appreciated that the word sticky is defined as the ability to stick to a surface and also the ability to secure one object to another. As used herein, the word sticky is intended to encompass any means of sticking to a surface and/or securing one object to another including, but not limited to, chemical adhesion, magnetic attraction, mechanical fastening, and material bonding.

Figure 6A:
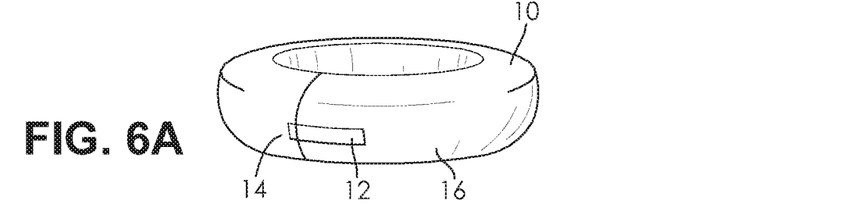
FIGS. 6A-6D: show the sticky portion 12 of the first soft cervical collar 10 attaching to an outer surface of the second end 16 (FIG. 6A); attaching to an inner surface of the second end 16 (FIG. 6B); the sticky portion 20 of the second soft cervical collar 18 attaching to an outer surface of the second end 24 (FIG. 6C); and attaching to an inner surface of the second end 24 (FIG. 6D) according to embodiments of the invention.
Figure 6B:
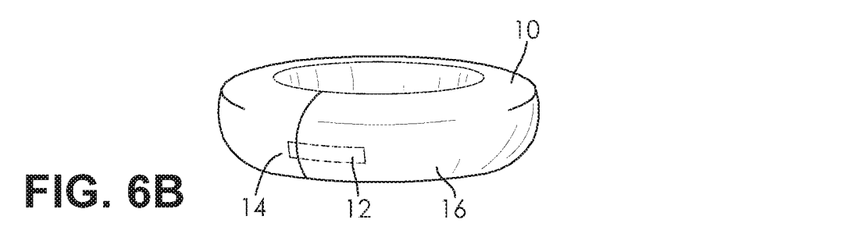
Figure 6C:
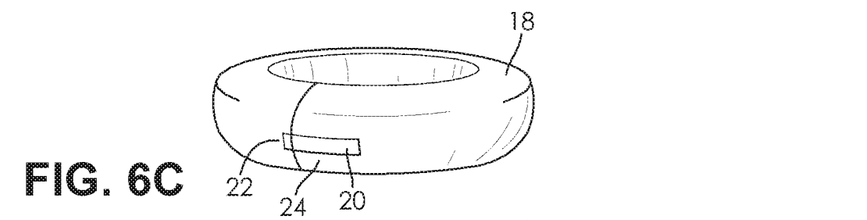
Figure 6D:
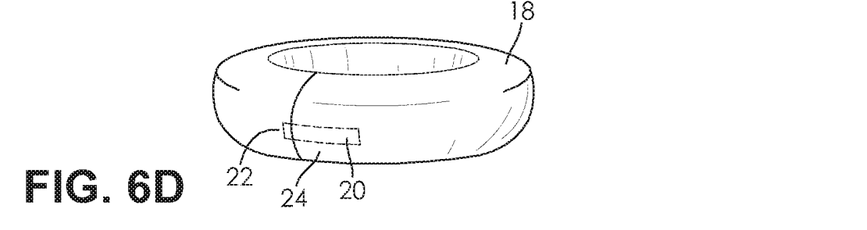

In embodiments of the present invention, the inventive method involves the steps of: placing a first soft cervical collar 10 around a neck of a wearer; securing the first soft cervical collar 10 around the neck of a wearer with a sticky portion 12 that extends from a first end 14 of the first soft cervical collar 10 and attaches to a second end 16 of the first soft cervical collar 10; placing a second soft cervical collar 18 surrounding the first soft cervical collar 10 with a sticky portion 20 that extends from a first end 22 of the second soft cervical collar 18 and attaches to a second end 24 of the second soft cervical collar 18. As shown in FIGS. 6A-6B, it is appreciated that the sticky portion 12 of the first soft cervical collar 10 attaches to an outer surface or an inner surface of the second end 16 of the first soft cervical collar according to some embodiments of the present invention. As shown in FIGS. 6C-6D, it is appreciated that the sticky portion 20 of the second soft cervical collar 18 attaches to an outer surface or an inner surface of the second end 24 of the second soft cervical collar 18.

Figure 3A:
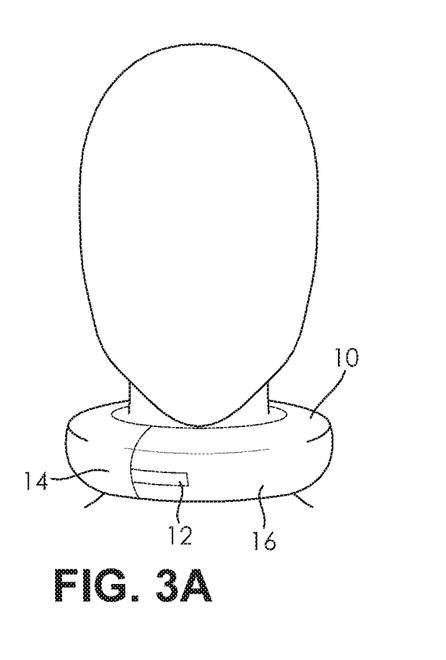
FIG. 3A: shows the first soft cervical collar 10 secured around the neck of a wearer in a reverse manner with the sticky portion 12 attached to the second end 16 at a front of the neck of a wearer according to embodiments of the invention
Figure 3B:
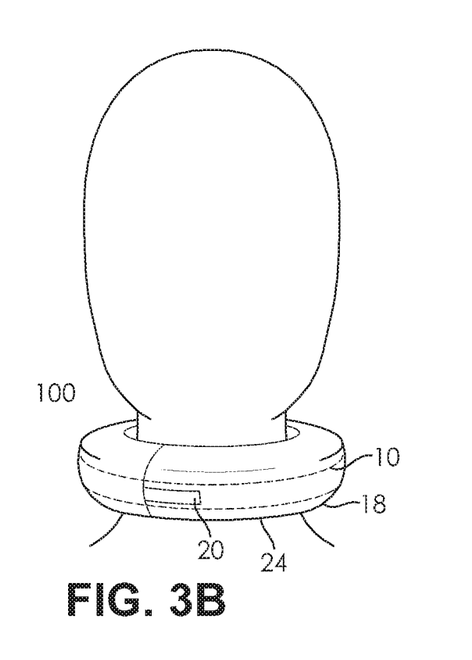
FIG. 3B: shows the second soft cervical collar 18 surrounding the first soft cervical collar 10 as shown in in FIG. 3A (shown in ghost), in a traditional manner with the sticky portion 20 attached to the second end 24 at a back of the neck of a wearer, forming a double soft collar 100 according to embodiments of the invention.

In one embodiment of the present invention and as shown in FIGS. 3A-3B, an inventive method of using a double soft cervical collar 100 includes: securing the first soft cervical collar 10 around the neck of a wearer in a reverse manner with the sticky portion 12 of the first soft cervical collar 10 attached to the second end 16 of the first soft cervical collar 10 at the front of the neck of a wearer; and securing the second soft cervical collar 18 surrounding the first soft cervical collar 10 in a traditional manner with the sticky portion 20 of the second soft cervical collar 18 attached to the second end 24 of the second soft cervical collar at a back of the neck of a wearer, forming a double soft cervical collar 100.

Figure 4A:
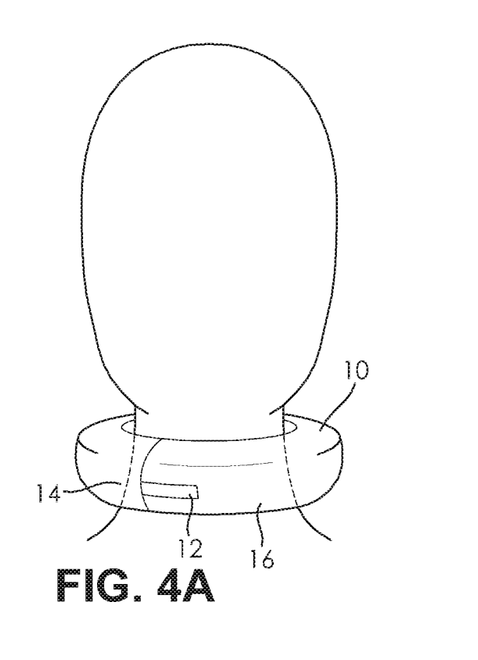
FIG. 4A: shows the first soft cervical collar 10 secured around the neck of a wearer in a traditional manner with the sticky portion 12 attached to the second end 16 at a back of the neck of a wearer according to embodiments of the invention
Figure 4B:
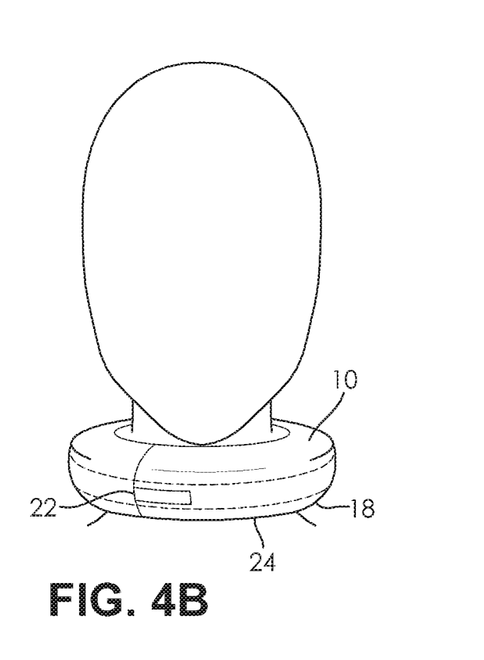
FIG. 4B: shows the second soft cervical collar 18 surrounding the first soft cervical collar 10 as shown in in FIG. 4A (shown in ghost), in a reverse manner with the sticky portion 20 attached to the second end 24 at a front of the neck of a wearer, forming a double soft collar 100 according to embodiments of the invention.

In another embodiment of the present invention and as shown in FIGS. 4A-4B, an inventive method of using a double soft cervical collar 100 includes: securing the first soft cervical collar 10 around the neck of a wearer in a traditional manner with the sticky portion 12 of the first soft cervical collar 10 attached to the second end 16 of the first soft cervical collar 10 at the back of the neck of a wearer; and securing the second soft cervical collar 18 surrounding the first soft cervical collar 10 in a reverse manner with the sticky portion 20 of the second soft cervical collar 18 attached to the second end 24 of the second soft cervical collar at a front of the neck of a wearer, forming a double soft cervical collar 100.

Figure 5A:
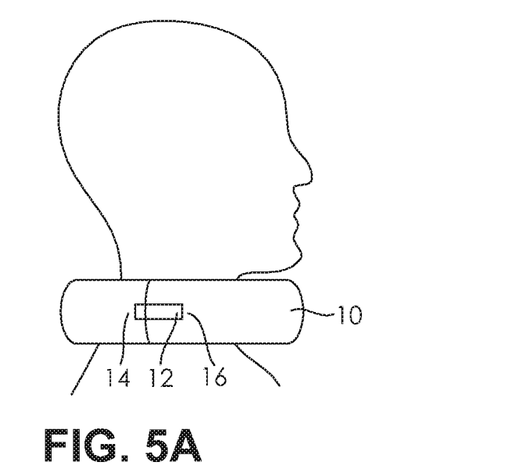
FIG. 5A: shows the first soft cervical collar 10 secured around the neck of a wearer in a first sideways manner with the sticky portion 12 attached to the second end 16 at a first side of the neck of a wearer, the first side being between the front and the back of the neck of a wearer according to embodiments of the invention.
Figure 5B:
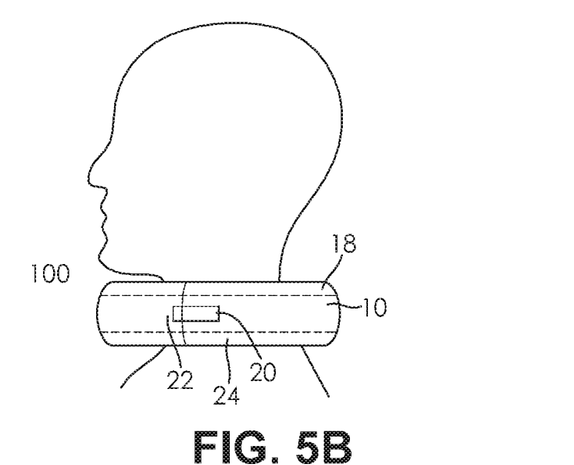
FIG. 5B: shows the second soft cervical collar 18 secured surrounding the first soft cervical collar 10 as shown in FIG. 5A (shown in host) in a second sideways manner with the sticky portion 20 attached to the second end 24 at a second side of the neck of a wearer, the second side being between the front and the back of the neck of a wearer opposite the first side, forming a double soft collar 100 according to embodiments of the invention.

In still another embodiment of the present invention and as shown in FIGS. 5A-5B, an inventive method of using a double soft cervical collar 100 includes: securing the first soft cervical collar 10 around the neck of a wearer in a first sideways manner with the sticky portion 12 of the first soft cervical collar 10 attached to the second end 16 of the first soft cervical collar 10 at a first side of the neck of a wearer, the first side being between the front and the back of the neck of a wearer; and securing the second soft cervical collar 18 surrounding the first soft cervical collar 10 in a second sideways manner with the sticky portion 20 of the second soft cervical collar 18 attached to the second end 24 of the second soft cervical collar at a second side of the neck of a wearer, the second side being between the front and the back of the neck of the wearer opposite the first side, forming a double soft cervical collar 100.

It is appreciated that in embodiments of the present invention the first soft cervical collar 10 and the second soft cervical collar 18 of the double soft cervical collar 100 are concentric. In other inventive embodiments it is appreciated that the first soft cervical collar 10 and the second soft cervical collar 18 of the double soft cervical collar 100 are not joined or attached together and instead the second soft cervical collar 18 is merely secured surrounding the first soft cervical collar 10 with the sticky portion 20 that extends from the first end 22 of the second soft cervical collar 18 and attaches to the second end 24 of the second soft cervical collar 18. It is further appreciated that the first soft collar 10 and the second soft collar 18 fully overlap in some inventive embodiments of the present invention, and partially overlap in other inventive embodiments of the present invention.

In some embodiments, and as described in further detail in the following description of the experimental method, the inventive method of using a double soft cervical collar 100 creates a subjective feeling of tightness and inability in moving the neck. In other embodiments, the subjective feeling of tightness perceived by the wearer of the double soft cervical collar 100 is equal to or greater than the subjective feeling of tightness perceived while wearing a hard collar, and the inability in moving the neck perceived by the wearer is equal to or greater than the inability in moving the neck perceived while wearing a hard collar.

In embodiments of the present invention, the sticky portions 12 and 20 of the first soft cervical collar 10 and the second soft cervical collar 18, respectively, may be a variety of shapes illustratively including rectangular, circular, triangular, cylindrical, or combinations thereof.

In some embodiments of the present invention, the sticky portions 12 and 20 of the first soft cervical collar 10 and the second soft cervical collar 18, respectively, have a length of between 5% and 70% of the length of the first soft cervical collar 10 and the second soft cervical collar 18, respectively. In other inventive embodiments, the sticky portions 12 and 20 of the first soft cervical collar 10 and the second soft cervical collar 18, respectively, have a length of between 10% and 50% of the length of the first soft cervical collar 10 and the second soft cervical collar 18, respectively.

In other embodiments of the present invention, the sticky portions 12 and 20 of the first soft cervical collar 10 and the second soft cervical collar 18, respectively, have a width of between 10% and 99% of the width of the first soft cervical collar 10 and the second soft cervical collar 18, respectively. In still other inventive embodiments, the sticky portions 12 and 20 of the first soft cervical collar 10 and the second soft cervical collar 18, respectively, have a width of between 20% and 80% of the width of the first soft cervical collar 10 and the second soft cervical collar 18, respectively.

In some inventive embodiments the first soft cervical collar 10 and the second cervical collar 18 are substantially rectangular in shape and have angled edges, are substantially cylindrical or tubular in shape and have rounded edges, or a combination thereof.

In another inventive embodiment, a method of using a double soft cervical collar 100 is provided and includes: positioning a first soft cervical collar 10 around a neck of a wearer; extending a sticky portion 12 of the first soft cervical collar 10 between a first end 14 and a second end 16 of the first soft cervical collar; attaching the first 14 and second 16 ends of the first soft cervical collar 10 together with the sticky portion 12 and securing the first soft cervical collar 10 around the neck of a wearer; positioning a second soft cervical collar 18 surrounding the first soft cervical collar 10; extending a sticky portion 20 of the second soft cervical collar 18 between a first end 22 and a second end 24 of the second soft cervical collar 18; and attaching the first 22 and second 24 ends of the second soft cervical collar 18 together with the sticky portion 20 and securing the second soft cervical collar 18 surrounding the first soft cervical collar 10.

In an inventive embodiment, a method of using a double soft cervical collar 100 includes: positioning the first soft cervical collar 10 in a reverse manner around the neck of the wearer with the sticky portion 12 of the first soft cervical collar 10 arranged at a front of the neck when the first 14 and second 16 ends of the first soft cervical collar 10 are attached together and secured around the neck of the wearer; and positioning the second soft cervical collar 18 surrounding the first soft cervical collar 10 in a traditional manner with the sticky portion 20 of the second soft cervical collar 18 arranged at a back of the neck when the first 22 and second 24 ends of the second soft cervical collar 18 are attached together and secured surrounding the first soft cervical collar 10.

In another inventive embodiment, a method of using a double soft cervical collar 100 includes: positioning the first soft cervical collar 10 in a traditional manner around the neck of the wearer with the sticky portion 12 of the first soft cervical collar 10 arranged at a back of the neck when the first 14 and second 16 ends of the first soft cervical collar 10 are attached together and secured around the neck of the wearer; and positioning the second soft cervical collar 18 surrounding the first soft cervical collar 10 in a reverse manner with the sticky portion 20 of the second soft cervical collar 18 arranged at a front of the neck when the first 22 and second 24 ends of the second soft cervical collar 18 are attached together and secured surrounding the first soft cervical collar 10.

In another embodiment of the present invention, the experimental method that shows the usefulness of the double soft collar 100 is disclosed, the experimental method comprising of the following steps:

A) Selection of Collars to be Compared:

The collars selected for the present invention were of four types—hard cervical collars, single soft cervical collars worn in a traditional manner (as shown in FIG. 4A), single soft cervical collars worn in a reverse manner (as shown in FIG. 3A), and the inventive double soft cervical collar 100 (as shown in FIGS. 3B, 4B, and 5B).

B) Selection of the Parameters to be Tested for:

The parameters that are tested in the present invention were the subjective feelings of tightness around the neck and inability to move the neck.

C) Selection of Subjects:

The subjects selected for the experimental method of the present invention were the ER residents and attending physicians willing to participate in the experiment recruited on a voluntary basis. The exclusion criteria applied while selecting the subjects include excluding the ER residents and attending physicians unwilling to participate and the volunteers with any neck pain due to trauma or unspecified origin. In the present invention, 18 residents were recruited.

D) Preparation of Score Sheet:

Based on the parameters which were being tested, a simple tabulated recording sheet for the participants was designed for each individual participant which consisted of subjective feelings of tightness around the neck and inability to move the neck as the parameters and scores ranging from 1 to 4 for each parameter which were meant to be circled.

E) Method of Experiment:

In the present invention, all the subjects selected were asked to wear the four collars one after the other. They were then asked to score their subjective feelings of tightness around the neck and inability to move the neck with regard to all the four cervical collars in the score sheets.

F) Recording the Results:

The results of the experiment of the present invention were recorded, tabulated and represented by means of graphs.

G) Description of Scores:

The scores in the experiment for the present invention ranged from 1 to 4, for each parameter which were described as follows:

Tightness around the neck upon wearing the 4 different cervical collars:

Score 1: No tightness.
Score 2: Slightly tight.
Score 3: Almost tight.
Score 4: Very tight.

Movement of the neck upon wearing the 4 different cervical collars:

Score 1: Movement of the neck freely.
Score 2: Movement of the neck with slight difficulty.
Score 3: Movement of the neck with great difficulty.
Score 4: No movement of the neck.

Figure 7:
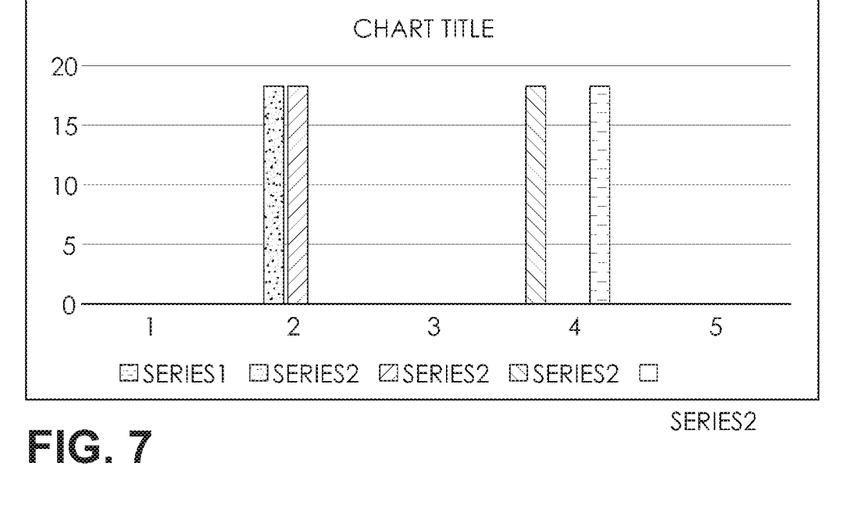
FIG. 7: shows the graph depicting the results of the experimental study done for the tightness of different collars around neck, with the number of participants on the vertical axis, and the score selected by the participants for each collar compared on the horizontal axis.

H) Tabulating Results for Tightness:

The results of the experiment conducted to compare the usefulness of the inventive double soft collar 100 in terms of tightness around the neck, were recorded into Table 1, and are shown in FIG. 7, as follows:

a) For Hard Cervical Collar: Tightness around the neck was scored 4 by all 18 participants (series 4).

b) For Single Soft Cervical Collar worn in Traditional Manner: Tightness around the neck was scored 2 by all 18 participants (series 2).

c) For Single Soft Cervical Collar worn in Reverse Manner: Tightness around the neck was scored 2 by all 18 participants (series 3).

d) For Double Soft Cervical Collar 100: Tightness around the neck was scored 4 by all 18 participants (series 1).

TABLE 1

| GROUPS | SCORE 1 | SCORE 2 | SCORE 3 | SCORE 4 |
|---|---|---|---|---|
| A | 0 | 0 | 0 | 18 |
| B | 0 | 18 | 0 | 0 |
| C | 0 | 18 | 0 | 0 |
| D | 0 | 0 | 0 | 18 |

Figure 8:
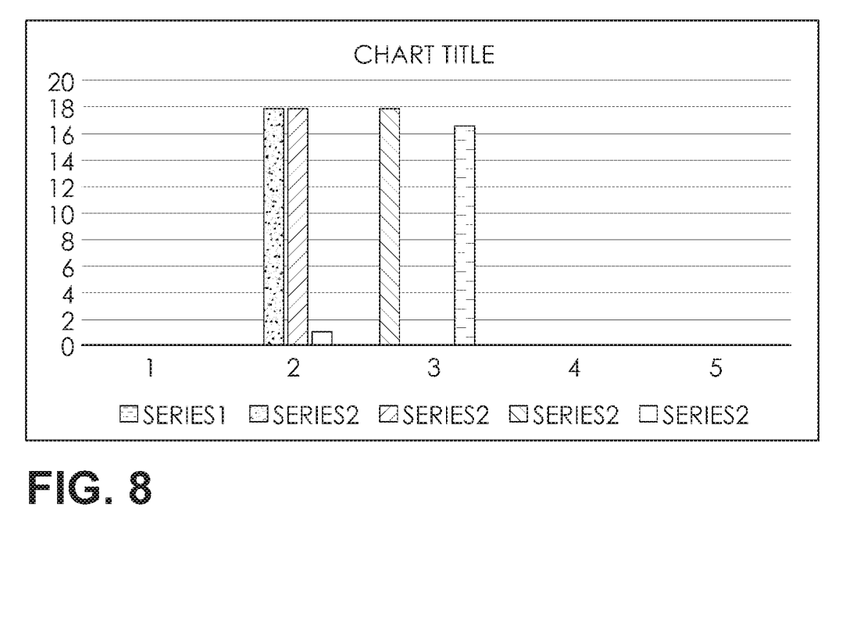
FIG. 8: shows the graph depicting the results of the experimental study done for the inability to move the neck with different collars around the neck, with the number of participants on the vertical axis, and the score selected by the participants for each collar compared on the horizontal axis.

Groups - A: Hard collar; B: soft collar—sticky portion to the back; C: soft collar—sticky portion to the front; D: double cervical collar
Scores - 1: no tightness; 2: slightly tight; 3: almost tight; 4: very tight I) Tabulating Results for Movement of Neck:

The results of the experiment conducted to compare the usefulness of the double soft collar 100 in terms of movement of the neck, were recorded into Table 2, and are shown in FIG. 8, as follows:

a) For Hard Cervical Collar: Movement of the neck was scored 3 by all 18 participants (series 4).

b) For Single Soft Cervical Collar worn in Traditional Manner: Movement of the neck was scored 2 by all 18 participants (series 2).

c) For Single Soft Cervical Collar worn in Reverse Manner: Movement of the neck was scored 2 by all 18 participants (series 3).

d) For Double Soft Cervical Collar: Movement of the neck was scored 3 by 17 participants (series 1) while 1 participant scored 2 (series 5).

TABLE 2

| GROUPS | SCORE 1 | SCORE 2 | SCORE 3 | SCORE 4 |
|---|---|---|---|---|
| A | 0 | 0 | 18 | 0 |
| B | 0 | 18 | 0 | 0 |
| C | 0 | 18 | 0 | 0 |
| D | 0 | 1 | 17 | 0 |

Groups - A: Hard collar; B: soft collar—sticky portion to the back; C: soft collar—sticky portion to the front; D: double cervical collar
Scores - 1: move the neck freely; 2: move the neck with slight difficulty; 3: move the neck with great difficulty; 4: cannot move the neck at all J) Analysis of the Results:

The values of the Chi-Square values and two tailed p-values after analysis were disclosed to be as follows:

a) Tightness around neck:
Chi-Square value is 24.
Two tailed p-value is 0.0001.

b) Inability to move the neck:
Chi-Square value is 58.7734.
Two tailed p-value is <0.0001.

K) Conclusions Drawn from the Experiment:

a) It is disclosed that the inventive double soft collar 100 has similar rigidity as shown by a hard cervical collar in regard to the inability to move the neck. The tightness of the inventive double soft collar 100 around the neck is also similar to the hard cervical collar.

b) The results of the experiment were compared and analysed for both tightness around the neck and movement of the neck after wearing the 4 different types of collars. The analysis was done using the Pearson Chi-Square analysis with two tailed p-value for both the subjective feelings.

c) It can be concluded from the experiment that the use of a single soft cervical collar is less effective than the use of a hard cervical collar and the inventive double soft cervical collar 100. It was also concluded from the experiment that the inventive double soft cervical collar 100 is at least as effective as the single hard cervical collar and thus the inventive double soft cervical collar 100 can be used in traumatic conditions with additional reinforcements according to the need and the type of trauma involved and impart at least the same amount of rigidity as a single hard cervical collar, and also impart at least the same amount of flexibility and comfort as a single soft cervical collar, while simultaneously minimizing the risk of secondary cervical collar related injury and adverse effects observed in the usage of single hard cervical collars illustratively including tissues ischemia, exacerbation of pain, and increased risk of aspiration.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. A method of using a double soft cervical collar comprising:
    placing a first soft cervical collar around a neck of a wearer;
    securing the first soft cervical collar around the neck of a wearer with a first sticky portion that extends from a first end of the first soft cervical collar and attaches to a second end of the first soft cervical collar;
    placing an inner surface of a second soft cervical collar entirely surrounding an outer surface of the first soft cervical collar; and
    securing the second soft cervical collar entirely surrounding the first soft cervical collar with a second sticky portion that extends from a first end of the second soft cervical collar and attaches to a second end of the second soft cervical collar.

2. The method of using a double soft cervical collar of claim 1 wherein the double soft cervical collar creates a subjective feeling of tightness and inability in moving the neck.

3. The method of using a double soft cervical collar of claim 2 wherein the subjective feeling of tightness perceived by the wearer is equal to or greater than a subjective feeling of tightness perceived while wearing a hard collar and the inability in moving the neck perceived by the wearer is equal to or greater than the inability in moving the neck perceived while wearing the hard collar.

4. The method of using a double soft cervical collar of claim 1 wherein the first and second sticky portions of the first and second soft cervical collars, respectively, have a length of between 5% and 70% the length of the first and the second soft cervical collar, respectively.

5. The method of using a double soft cervical collar of claim 4 wherein the first and second sticky portions of the first and second soft cervical collars, respectively, have a length of between 10% and 50% the length of the first and the second soft cervical collar, respectively.

6. The method of using a double soft cervical collar of claim 1 further comprising:
    securing the first soft cervical collar around the neck of the wearer in a reverse manner with the first sticky portion of the first soft cervical collar attached to the second end of the first soft cervical collar at a front of the neck of the wearer; and
    securing the second soft cervical collar surrounding the first soft cervical collar in a traditional manner with the second sticky portion of the second soft cervical collar attached to the second end of the second soft cervical collar at a back of the neck of the wearer.

7. The method of using a double soft cervical collar of claim 1 further comprising:
    securing the first soft cervical collar around the neck of the wearer in a traditional manner with the first sticky portion of the first soft cervical collar attached to the second end of the first soft cervical collar at a back of the neck of the wearer; and
    securing the second soft cervical collar surrounding the first soft cervical collar in a reverse manner with the second sticky portion of the second soft cervical collar attached to the second end of the second soft cervical collar at a front of the neck of the wearer.

8. The method of using a double soft cervical collar of claim 1 further comprising:
    securing the first soft cervical collar around the neck of the wearer in a first sideways manner with the first sticky portion of the first soft cervical collar attached to the second end of the first soft cervical collar at a first side of the neck of the wearer, said first side being between the front and the back of the neck of the wearer; and
    securing the second soft cervical collar surrounding the first soft cervical collar in a second sideways manner with the second sticky portion of the second soft cervical collar attached to the second end of the second soft cervical collar at a second side of the neck of the wearer, said second side being between the front and the back of the neck of the wearer opposite said first side.

9. The method of using a double soft cervical collar of claim 1 wherein the first sticky portion of the first soft cervical collar attaches to the outer surface of the second end of the first soft cervical collar.

10. The method of using a double soft cervical collar of claim 1 wherein the first sticky portion of the first soft cervical collar attaches to an inner surface of the second end of the first soft cervical collar.

11. The method of using a double soft cervical collar of claim 1 wherein the second sticky portion of the second soft cervical collar attaches to an outer surface of the second end of the second soft cervical collar.

12. The method of using a double soft cervical collar of claim 1 wherein the second sticky portion of the second soft cervical collar attaches to the inner surface of the second end of the second soft cervical collar.

13. The method of using a double soft cervical collar of claim 1 wherein the first and second sticky portions of the first and second soft cervical collars, respectively, are rectangular, circular, triangular, cylindrical, or combinations thereof.

14. The method of using a double soft cervical collar of claim 1 wherein the first and second sticky portions of the first and second soft cervical collars, respectively, have a width of between 10% and 99% the width of the first and the second soft cervical collar, respectively.

15. The method of using a double soft cervical collar of claim 1 wherein the first and second sticky portions of the first and second soft cervical collars, respectively, have a width of between 20% and 80% the width of the first and the second soft cervical collar, respectively.

16. The method of using a double soft cervical collar of claim 1 wherein the first soft cervical collar and the second soft cervical collar have angled edges, rounded edges, or a combination thereof.

17. A method of using a double soft cervical collar comprising:
- positioning an inner surface of a first soft cervical collar around a neck of a wearer;
- extending a first sticky portion of the first soft cervical collar between a first end and a second end of the first soft cervical collar;
- attaching the first and second ends of the first soft cervical collar together with the first sticky portion and securing the first soft cervical collar around the neck of the wearer;
- positioning an inner surface of a second soft cervical collar entirely surrounding an outer surface of the first soft cervical collar;
- extending a second sticky portion of the second soft cervical collar between a first end and a second end of the second soft cervical collar; and
- attaching the first and second ends of the second soft cervical collar together with the second sticky portion and securing the second soft cervical collar entirely surrounding the first soft cervical collar.

18. The method of using a double soft cervical collar of claim 17 further comprising:
- positioning the first soft cervical collar in a reverse manner around the neck of the wearer with the first sticky portion of the first soft cervical collar arranged at a front of the neck when the first and second ends of the first soft cervical collar are attached together and secured around the neck of the wearer; and
- positioning the second soft cervical collar surrounding the first soft cervical collar in a traditional manner with the second sticky portion of the second soft cervical collar arranged at a back of the neck when the first and second ends of the second soft cervical collar are attached together and secured surrounding the first soft cervical collar.

19. The method of using a double soft cervical collar of claim 17 further comprising:
- positioning the first soft cervical collar in a traditional manner around the neck of the wearer with the first sticky portion of the first soft cervical collar arranged at a back of the neck when the first and second ends of the first soft cervical collar are attached together and secured around the neck of the wearer; and
- positioning the second soft cervical collar surrounding the first soft cervical collar in a reverse manner with the second sticky portion of the second soft cervical collar arranged at a front of the neck when the first and second ends of the second soft cervical collar are attached together and secured surrounding the first soft cervical collar.

20. The method of using a double soft cervical collar of claim 17 wherein the first soft cervical collar and the second soft cervical collar have angled edges, rounded edges, or a combination thereof.

* * * * *